US012628751B2

(12) United States Patent
Hamelink et al.

(10) Patent No.: US 12,628,751 B2
(45) Date of Patent: May 19, 2026

(54) TBRFV RESISTANT TOMATO PLANT

(71) Applicant: RIJK ZWAAN ZAADTEELT EN ZAADHANDEL B.V., De Lier (NL)

(72) Inventors: Roel Hamelink, De Lier (NL); Jonathan Kalisvaart, De Lier (NL); Hamed Rashidi, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 617 days.

(21) Appl. No.: 16/975,523

(22) PCT Filed: Dec. 8, 2017

(86) PCT No.: PCT/EP2017/082096
§ 371 (c)(1),
(2) Date: Aug. 25, 2020

(87) PCT Pub. No.: WO2019/110130
PCT Pub. Date: Jun. 13, 2019

(65) Prior Publication Data
US 2022/0389442 A1      Dec. 8, 2022

(51) Int. Cl.
| *A01H 5/08* | (2018.01) |
| *A01H 1/00* | (2006.01) |
| *A01H 1/04* | (2006.01) |
| *A01H 6/82* | (2018.01) |
| *C12N 15/82* | (2006.01) |

(52) U.S. Cl.
CPC ............. *A01H 1/126* (2021.01); *A01H 1/045* (2021.01); *A01H 5/08* (2013.01); *A01H 6/825* (2018.05); *C12N 15/8283* (2013.01)

(58) Field of Classification Search
None
See application file for complete search history.

(56) References Cited

FOREIGN PATENT DOCUMENTS

WO      2013/064641 A1      5/2013

OTHER PUBLICATIONS

Bolger et al. GenEmbl Database, Acc. No. HG975450, DBLink Bioproject PRJEB5809 Biosample SAMEA3283146, Nov. 17, 2015.*
Li et al., GenEmbl Database, Acc. No. CP023767, Nov. 3, 2017.*
Shirasawa et al., GenEmbl Database, Acc. No. AP028945, Nov. 3, 2023.*
Li et al., GenEmbl Database, Acc. No. CP023768, Nov. 3, 2017.*
Aoki et al., GenEmbl Database, Acc. No. AK322140, BMC genomics 11, 210, 2010.*

(Y) Aoki et al., GenEmbl Database, Acc. No. AK321182, BMC Genomics 1, 210, 2010.*
(Z) Bolger et al., GenEmbl Database, Acc. No. HG975450, Nov. 17, 2015, positions 7383021-7383221.*
(UU) Bolger et al., GenEmbl Database, Acc. No. HG975450, Nov. 17, 2015, positions 3931275-3931475.*
Database EMBL: Accession No. CP023767 Solanum Lycopersium Cultivar I-3 Chromosome 11, Nov. 20, 2017.
Database EMBL: Accession No. CP023768 Solanum Lycopersium Cultivar I-3 Chromosome 12, Nov. 20. 2017.
Ann Maree Catanzariti, et al., The tomato I-3 gene: a novel gene for resistance to Fusarium wilt disease, New Phytologist (2015) 207:106-118.
P. Kadirvel, et al, Mapping of QTLs in tomato line FLA456 associated with resistance to a virus causing tomato yellow leaf curl disease, Euphytica (2013) 190:297-308.
Neta Luria, et al., A New Israeli Tobamovirus Isolate Infects Tomato Plants Harboring Tm-22 Resistance Genes, PLoS One (Jan. 20, 2017) DOI:10.1371/journal.pone.0170429.
N. Salem, et al., A new tobamovirus infecting tomato crops in Jordan, Arch Virol (2016) 161:503-506.
Ainong Shi, et al., Molecular Markers for Tm-2 Alleles of Tomato Mosaic Virus Resistance in Tomato, American Journal of Plant Sciences (2011) 2:180-189.
Wojciech Szczechura, et al., Tomato Molecular Markers, Vegetable Crops Research Bulletin (2011) vol. 74, 5-23.
International Search Report mailed May 29, 2018 in International Application No. PCT/EP2017/082096.
The Tomato Genome Consortium: Letter: The tomato genome sequence provides insights into fleshy fruit evolution, Nature (May 31, 2012) vol. 485, p. 635-641.

* cited by examiner

*Primary Examiner* — Phuong T Bui
(74) *Attorney, Agent, or Firm* — Duane Morris LLP; Thomas J. Kowalski

(57)      ABSTRACT

The invention relates to a *Solanum lycopersicum* plant that is resistant to TBRFV, which plant comprises a QTL on chromosome 11, and/or a QTL on chromosome 12, and/or a QTL on chromosome 6. The presence of the QTL on chromosome 11 can be identified by use of at least one of the markers selected from the group comprising SEQ ID NOS: 1, 9, and 2-8; the presence of the QTL on chromosome 12 can be identified by use of at least one of the markers selected from the group comprising SEQ ID NOS: 10, 15, and 11-14; and the presence of the QTL on chromosome 6 can be identified by use of at least one of the markers selected from the group comprising SEQ ID NOS: 16, 25, and 17-24. The QTL is as comprised in the genome of a *Solanum lycopersicum* plant representative seed of which was deposited with the NCIMB under deposit number NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890.

4 Claims, 4 Drawing Sheets

Specification includes a Sequence Listing.

Fig.1-1

Marker sequences SEQ ID Nos. 1-25

SEQ ID No. 1

TTTATGGGACGTTGAGCATCTCATGAACTTACGGAGATTTCTAGTTGAGTTGTGTGATCAAGTGGTAGATTTAA
CGTTGTGTACTATCTCTAAAAGCTTGGTCTTACCAAGAGGAATTTATCGTCTTCCTACACTTGAAGTCGAGAATT
TGGAACTGTCTTATAGTGATATTACAACCGCGACATATTCATTTTACTATGA

SEQ ID No. 2

ACACATTAATAAGTTTCAAGTACCGATAAAGGCAAATTTTTATCATGGGTTAGCAAAGCAAGATGAGTAAGGT
ATCTGTAGAATTAGATATACTCAACCATGTCTAAAAGGTGTGTCACTTTCAGATGCCTACATTTACCGAAAAAA
GATAATCTTGCTTTTATGGGCTTTAACCAAATACACAAGAATGGGATGCAACAG

SEQ ID No. 3

AGAAACAACCCCTCTACCTAACACAAGGTATGTGTAAGGTCTAAGTAGACTCTACTATACTAGATATGTTATTG
TTGTTGAGAAATGTAATATGAGGGTCGGAAACATCCACTCTACCTAACACAAGGTATGTGTAAGGTCTACATA
GACTATTATACTGAATATGTTATTGTTGTTGAGAAATGTAATCTGAGGGTCGGA

SEQ ID No. 4

GAGAGAGCGAATCTGCAAAGCTGATTTCCGATGCTACTGCGGCTGCTGGAATGGGTTTGATTGAGCTGAGGA
GGATTGAAGCTTCTAGAGAAGTTGCTGGGACTTTGGCTAAGACTCCTAATGTTGCTTACTTGCCTAAGCAAGG
GAATATGCTTCTTGGACTCGGCCGTTGAGTAGGTAATCAATTGAGCAAAATGCTAG

SEQ ID No. 5

GATGGATTCGTAAATTCAATACGTGATTCCAAGATAAGCATGTTAATTTTAGGAAAAAAATCTTCAATTTTCTTT
TACCATTTTTCTTTCTTTGGGTGGAAAGATTCCTCGTCTTCAAATGGAAATACTAAACGAAATGTTACTTTGACA
AAAGAACGTTCCTTCTCTTTTGGAGGAATGACTTCATTATGATAGTGGACT

SEQ ID No. 6

AGTAAAGGAAACTCCTGAGTTTTGTGGCTTTTAAATTAAGGATATGTAGAATGTACCAAAATGCTTTTTAATCTT
GTGGTATTACTCATGTTAGTCGGAGGCGAACTAAAAGAGAAAGTAAGATGAAGCATAATCAAGTTCACTAGTC
ATTTGCTTCCACTTTGGACTACGGAAGTCGATCATTAGGGATAGAATATTACT

SEQ ID No. 7

GGGAGTTGCCTTGTTCTATTCAGAGACTTACCATAAACAATCTGAAAACATTAAGCAGCCAAGTTCTGAAAAGC
CTCACCTCTCTTCAATATCTACGCGTTGAGGGTACTATACCTCGAATTCAGTCACAAGGTGGACTTCCCTCCTCT
CTTTCTCAGCTACATTTAGGATACCATGATGAGCTCCATTCACTACATCTTT

Fig.1-2

SEQ ID No. 8

CCTGAAGAAGCCTCCATGGCGAATTGGGCCAGCGGATGGGATCAGCAAGTTGAATGGAGGATATAGTTCCCA
TGAACCAACTGATTCGAGAAGAATCCTCGGTTTCAAAAGCCATTTTGAACCTCATTCCTGAGCACCATTGAATC
CTCATTGCAGCATTCACTGAAGATGCCCTAACACAAAATTCTGGTGTGTTTGCAC

SEQ ID No. 9

TAAAGTAGCGTGTAACCATTGGTGATGCATGTAAAGGGAATTTTCTAAATACAATCATTTTTTCTTCAAAGTTAA
CCATTTGTAGCTTTAACTGTTCAATAGCCTTGCACATAAGGTGTATCCTTCTTGGCCCTCTGTTTAGACAAAGTA
CCATCAATAGGATGAGAGTTACAGAAAAAAGTAGCAGAAGTACTTCTCAGA

SEQ ID No. 10

TGGTGTTGATCGGCGATTCCGGCGTCGGGAAATCTAATCTTCTATCCAGATTTACACGTAACGAGTTCAGTTTG
GAGTCAAAGTCAACGATCGGCGTTGAATTCGCTACTC

SEQ ID No. 11

CAAACAATGTGGATCAATTCGGGATCCAATGTCCGAATCAGACGTTAAATCTCGGGTTCAGGCAGTAGAGGAT
ACTGGAAAGTAAGAAAAGTTGTAGCTCGAAATCTGAATGCCAGTATAC

SEQ ID No. 12

GGTATGGGTGGTATGTTTGGTGGTGGAGACAAGTAAACATGAAAGCACAATTAGCAGTTGAAACTCAAAGCT
GGCAAATCTTTTTTCTTTTTTTTGTTAACTGGTAAAGAA

SEQ ID No. 13

CAATCAATTTGGTGCACAAGAACCAGGGAGCAACGATGAGATCGTAGAATTTGCTTGTACGCGTTTCAAGTCA
GAGTTCCCCATCTTTGACAAGATTGAAGTGAACGGCGAAAACACATCT

SEQ ID No. 14

TTGGGCCTAACTTAATCCCAAAAGCGTTCAAAAGATGAGAATTGTTCAAGACCATAAAAAAACAACCAAATTTCC
TAAACCTACTGATGTGGGACTCTTAACAGTAATATCTTTAAGAGATC

SEQ ID No. 15

TGTACGAAGACATATGAAATTCGGGATTCCCAAGGAGTAGTCTGGATATGGATGTCTCATAGAACACCACCTA
ATATTAACAAAATCCCCTGGTTTGAAAATTTTGAGAGGAAAGGATTTC

Fig.1-3

SEQ ID No. 16

ATCCTTAGGATGCTGCCGATTTGGGCTGCAGGGATGTTACATTTTGCTTCACATTCACATGTAAGCAGCTTTAC
AATCCAACAGGCGCGAAGTATGGATCATCATCTATCCCACAGCTTCCAAATACCTCCAGCCAGCATGTCTATTTT
TAGTGTCCTAACGGTGCTCATTGGCTTAGCGCTTTATGAGCGCTTCTTTGTT

SEQ ID No. 17

TTAAGCAGCATGTAGGAGCAGATCCTCATATCTATACTTCTGAGAACCCCACTATTCCGGCACCTCTGGACAGT
CAGCTACAT

SEQ ID No. 18

TTTAAGTTTTGCACGCCCTTCGTAAAATGTCTGACTCCACTACTACACCCNAGGTCTCTTCTCATTGAGCAGATT
CAATATATAGAAATGACCAYAAGTAAAAKWAACAT

SEQ ID No. 19

AATTTCTTKAAGCTACTCACATGGTGCAAGTCCCGTTGRCCTTGTTCAAGCTCCAAAGTTATATGGCTAAACAAT
ACATACGGGATACAACAATTACTTCTCAAAATGGTGCTGACACTTG

SEQ ID No. 20

GTAATGTGCATGGTAGCAAGTGACACCCTGTTGCTCATGCTTGAAGGTTTGGCTGATTTGGAAGTTGCAGCTTT
CTTTGCACTGCCATTAAGGCTAATGTGCTTGGGATTGTCAAATTAGATATTCCTGTTGCWCTTAGTGCTTTGGT
TAGTGCTTGTGCTAAGAAAGTTCCCACAGGTTTCAAGTGTGGTTAATTAGAG

SEQ ID No. 21

AGATGTAATCGATTCATTACAAATCAAATACTTTGTATTCTAGTTTTAATGATTTTGGTTTTTCAATCATATCTTTT
GTATTGTAATCATAATAGATTCATGAAGGAAAGAATAAGATCAT

SEQ ID No. 22

ATAAGGTTGATTTTGCAAAAGAGTGACCAAAATCCTCATCAGTGTAACCAAGCAGAGAAGCTGAAAACAAATG
AGAGACAAGGTAGGCAACAGAAAATTGAAGCTTAA

SEQ ID No. 23

ATTTTTKGGRARGTATTTTCCGTAGAAAACAATTTACATCACCAAACACAACATATTCAAATATATTTTCCATTTT
ACCCAAATAATTGTATTTCTGCAG

Fig.1-4

SEQ ID No. 24

TAAGGTGAAGCCTTTTGTGGATCCGCATCAAAAGGGTTGAGACTTTTTTTTCTTCTTTCTTGTTGTGCTAGTATTC
TGGGTTTCGGTTTGAGATTTGAGTTGTTGTTTTTTTTCAACCC

SEQ ID No. 25

CTTTACATCATTAGCATCCGAGTCCTGGTCATGAGCCAATGTTCGACCTTGACCTCAAGTAGKGTTGGGTCTATT
TCGAGTCAGGATAGGGTCTTGAGGCGAGTTGGAAGACGGAAGTCAAATTTGAGATCTTGAATTGGAGTCAAG
AGTCAAGTCTTATATCGAGTTTACACATAGAGAATTAGATTTTAAATAGAGATC

SEQUENCE LISTING

<160> NUMBER OF SEQ ID NOS: 25

<210> SEQ ID NO 1
<211> LENGTH: 201
<212> TYPE: DNA
<213> ORGANISM: Solanum lycopersicum

<400> SEQUENCE: 1

```
tttatgggac gttgagcatc tcatgaactt acggagattt ctagttgagt tgtgtgatca      60
agtggtagat ttaacgttgt gtactatctc taaaagcttg gtcttaccaa gaggaattta     120
tcgtcttcct acacttgaag tcgagaattt ggaactgtct tatagtgata ttacaaccgc     180
gacatattca ttttactatg a                                              201
```

<210> SEQ ID NO 2
<211> LENGTH: 201
<212> TYPE: DNA
<213> ORGANISM: Solanum lycopersicum

<400> SEQUENCE: 2

```
acacattaat aagtttcaag taccgataaa ggcaaatttt tatcatgggt tagcaaagca      60
agatgagtaa ggtatctgta gaattagata tactcaacca tgtctaaaag gtgtgtcact     120
ttcagatgcc tacatttacc gaaaaaagat aatcttgctt ttatgggctt taaccaaata     180
cacaagaatg ggatgcaaca g                                              201
```

<210> SEQ ID NO 3
<211> LENGTH: 201
<212> TYPE: DNA
<213> ORGANISM: Solanum lycopersicum

<400> SEQUENCE: 3

```
agaaacaacc cctctaccta acacaaggta tgtgtaaggt ctaagtagac tctactatac      60
tagatatgtt attgttgttg agaaatgtaa tatgagggtc ggaaacatcc actctaccta     120
acacaaggta tgtgtaaggt ctacatagac tattatactg aatatgttat tgttgttgag     180
aaatgtaatc tgagggtcgg a                                              201
```

<210> SEQ ID NO 4
<211> LENGTH: 201
<212> TYPE: DNA
<213> ORGANISM: Solanum lycopersicum

<400> SEQUENCE: 4

-continued

```
gagagagcga atctgcaaag ctgatttccg atgctactgc ggctgctgga atgggtttga      60
ttgagctgag gaggattgaa gcttctagag aagttgctgg gactttggct aagactccta     120
atgttgctta cttgcctaag caagggaata tgcttcttgg actcggccgt tgagtaggta     180
atcaattgag caaaatgcta g                                               201

<210> SEQ ID NO 5
<211> LENGTH: 201
<212> TYPE: DNA
<213> ORGANISM: Solanum lycopersicum

<400> SEQUENCE: 5
gatggattcg taaattcaat acgtgattcc aagataagca tgttaatttt aggaaaaaaa      60
tcttcaattt tcttttacca tttttctttc tttgggtgga aagattcctc gtcttcaaat     120
ggaaatacta aacgaaatgt tactttgaca aaagaacgtt ccttctcttt tggaggaatg     180
acttcattat gatagtggac t                                               201

<210> SEQ ID NO 6
<211> LENGTH: 201
<212> TYPE: DNA
<213> ORGANISM: Solanum lycopersicum

<400> SEQUENCE: 6
agtaaaggaa actcctgagt tttgtggctt ttaaattaag gatatgtaga atgtaccaaa      60 atgctttta atcttgtggt attactcatg ttagtcggag gcgaactaaa agagaaagta     120
agatgaagca taatcaagtt cactagtcat ttgcttccac tttggactac ggaagtcgat     180
cattagggat agaatattac t                                               201

<210> SEQ ID NO 7
<211> LENGTH: 201
<212> TYPE: DNA
<213> ORGANISM: Solanum lycopersicum

<400> SEQUENCE: 7
gggagttgcc ttgttctatt cagagactta ccataaacaa tctgaaaaca ttaagcagcc      60
aagttctgaa aagcctcacc tctcttcaat atctacgcgt tgagggtact atacctcgaa     120
ttcagtcaca aggtggactt ccctcctctc tttctcagct acatttagga taccatgatg     180
agctccattc actacatctt t                                               201

<210> SEQ ID NO 8
<211> LENGTH: 201
<212> TYPE: DNA
<213> ORGANISM: Solanum lycopersicum

<400> SEQUENCE: 8
cctgaagaag cctccatggc gaattgggcc agcggatggg atcagcaagt tgaatggagg      60
atatagttcc catgaaccaa ctgattcgag aagaatcctc ggtttcaaaa gccattttga     120
acctcattcc tgagcaccat tgaatcctca ttgcagcatt cactgaagat gccctaacac     180
aaaattctgg tgtgtttgca c                                               201

<210> SEQ ID NO 9
<211> LENGTH: 201
<212> TYPE: DNA
<213> ORGANISM: Solanum lycopersicum
```

<400> SEQUENCE: 9
taaagtagcg tgtaaccatt ggtgatgcat gtaaagggaa ttttctaaat acaatcattt     60
tttcttcaaa gttaaccatt tgtagcttta actgttcaat agccttgcac ataaggtgta    120
tccttcttgg ccctctgttt agacaaagta ccatcaatag gatgagagtt acagaaaaaa    180
gtagcagaag tacttctcag a                                              201

<210> SEQ ID NO 10
<211> LENGTH: 111
<212> TYPE: DNA
<213> ORGANISM: Solanum lycopersicum

<400> SEQUENCE: 10
tggtgttgat cggcgattcc ggcgtcggga aatctaatct tctatccaga tttacacgta     60
acgagttcag tttggagtca aagtcaacga tcggcgttga attcgctact c              111

<210> SEQ ID NO 11
<211> LENGTH: 121
<212> TYPE: DNA
<213> ORGANISM: Solanum lycopersicum

<400> SEQUENCE: 11
caaacaatgt ggatcaattc gggatccaat gtccgaatca gacgttaaat ctcgggttca     60
ggcagtagag gatactggaa agtaagaaaa gttgtagctc gaaatctgaa tgccagtata    120
c                                                                    121

<210> SEQ ID NO 12
<211> LENGTH: 110
<212> TYPE: DNA
<213> ORGANISM: Solanum lycopersicum

<400> SEQUENCE: 12
ggtatgggtg gtatgtttgg tggtggagac aagtaaacat gaaagcacaa ttagcagttg     60
aaactcaaag ctggcaaatc ttttttcttt ttttgttaac tggtaaagaa                110

<210> SEQ ID NO 13
<211> LENGTH: 121
<212> TYPE: DNA
<213> ORGANISM: Solanum lycopersicum

<400> SEQUENCE: 13
caatcaattt ggtgcacaag aaccagggag caacgatgag atcgtagaat ttgcttgtac     60
gcgtttcaag tcagagttcc ccatctttga caagattgaa gtgaacggcg aaaacacatc    120
t                                                                    121

<210> SEQ ID NO 14
<211> LENGTH: 121
<212> TYPE: DNA
<213> ORGANISM: Solanum lycopersicum

<400> SEQUENCE: 14
ttgggcctaa cttaatccca aaagcgttca aaagatgaga attgttcaag accataaaaa     60
acaaccaaat ttcctaaacc tactgatgtg ggactcttaa cagtaatatc tttaagagat    120
c                                                                    121

<210> SEQ ID NO 15
<211> LENGTH: 121

```
<212> TYPE: DNA
<213> ORGANISM: Solanum lycopersicum

<400> SEQUENCE: 15
tgtacgaaga catatgaaat tcgggattcc caaggagtag tctggatatg gatgtctcat      60
agaacaccac ctaatattaa caaaatcccc tggtttgaaa attttgagag gaaaggattt     120
c                                                                     121

<210> SEQ ID NO 16
<211> LENGTH: 201
<212> TYPE: DNA
<213> ORGANISM: Solanum lycopersicum

<400> SEQUENCE: 16
atccttagga tgctgccgat ttgggctgca gggatgttac attttgcttc acattcacat      60
gtaagcagct ttacaatcca acaggcgcga agtatggatc atcatctatc ccacagcttc     120
caaatacctc cagccagcat gtctattttt agtgtcctaa cggtgctcat tggcttagcg     180
ctttatgagc gcttctttgt t                                               201

<210> SEQ ID NO 17
<211> LENGTH: 83
<212> TYPE: DNA
<213> ORGANISM: Solanum lycopersicum

<400> SEQUENCE: 17
ttaagcagca tgtaggagca gatcctcata tctatacttc tgagaacccc actattccgg      60
cacctctgga cagtcagcta cat                                              83

<210> SEQ ID NO 18
<211> LENGTH: 110
<212> TYPE: DNA
<213> ORGANISM: Solanum lycopersicum
<220> FEATURE:
<221> NAME/KEY: misc_feature
<222> LOCATION: 51
<223> OTHER INFORMATION: /note="n = a or t or c or g"

<400> SEQUENCE: 18
tttaagtttt gcacgccctt cgtaaaatgt ctgactccac tactacaccc naggtctctt      60
ctcattgagc agattcaata tatagaaatg accayaagta aaakwaacat               110

<210> SEQ ID NO 19
<211> LENGTH: 121
<212> TYPE: DNA
<213> ORGANISM: Solanum lycopersicum

<400> SEQUENCE: 19
aatttcttka agctactcac atggtgcaag tcccgttgrc cttgttcaag ctccaaagtt      60
atatggctaa acaatacata cgggatacaa caattacttc tcaaaatggt gctgacactt     120
g                                                                     121

<210> SEQ ID NO 20
<211> LENGTH: 200
<212> TYPE: DNA
<213> ORGANISM: Solanum lycopersicum

<400> SEQUENCE: 20
gtaatgtgca tggtagcaag tgacaccctg ttgctcatgc ttgaaggttt ggctgatttg      60
```

-continued

```
gaagttgcag ctttctttgc actgccatta aggctaatgt gcttgggatt gtcaaattag        120
atattcctgt tgcwcttagt gctttggtta gtgcttgtgc taagaaagtt cccacaggtt        180
tcaagtgtgg ttaattagag                                                    200

<210> SEQ ID NO 21
<211> LENGTH: 121
<212> TYPE: DNA
<213> ORGANISM: Solanum lycopersicum

<400> SEQUENCE: 21
agatgtaatc gattcattac aaatcaaata ctttgtattc tagttttaat gattttggtt         60
tttcaatcat atcttttgta ttgtaatcat aatagattca tgaaggaaag aataagatca        120
t                                                                        121

<210> SEQ ID NO 22
<211> LENGTH: 108
<212> TYPE: DNA
<213> ORGANISM: Solanum lycopersicum

<400> SEQUENCE: 22
ataaggttga ttttgcaaaa gagtgaccaa aatcctcatc agtgtaacca agcagagaag         60
ctgaaaacaa atgagagaca aggtaggcaa cagaaaattg aagcttaa                     108

<210> SEQ ID NO 23
<211> LENGTH: 101
<212> TYPE: DNA
<213> ORGANISM: Solanum lycopersicum

<400> SEQUENCE: 23
atttttkggr argtattttc cgtagaaaac aatttacatc accaaacaca acatattcaa         60
atatattttc cattttaccc aaataattgt attttctgca g                           101

<210> SEQ ID NO 24
<211> LENGTH: 121
<212> TYPE: DNA
<213> ORGANISM: Solanum lycopersicum

<400> SEQUENCE: 24
taaggtgaag cctttttgtg gatccgcatc aaaagggttg agactttttt tttcttcttt         60
cttgttgcta gtattctggg tttcggtttt gagattttga gttgttgttt tttttcaacc        120
c                                                                        121

<210> SEQ ID NO 25
<211> LENGTH: 201
<212> TYPE: DNA
<213> ORGANISM: Solanum lycopersicum

<400> SEQUENCE: 25
ctttacatca ttagcatccg agtcctggtc atgagccaat gttcgacctt gacctcaagt         60
agkgttgggt ctatttcgag tcaggatagg gtcttgaggc gagttggaag acggaagtca        120
aatttgagat cttgaattgg agtcaagagt caagtcttat atcgagttta cacatagaga        180
attagatttt aaatagagat c                                                  201
```

TBRFV RESISTANT TOMATO PLANT

CROSS-REFERENCE TO RELATED APPLICATIONS

This application is a 371 of US National Phase application of international patent application Serial No. PCT/EP2017/082096 filed Dec. 8, 2017, which published as PCT Publication No. WO WO2019/110130 on Jun. 13, 2019.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING STATEMENT

The instant application contains a Sequence Listing which has been submitted electronically and is hereby incorporated by reference in its entirety. Said ASCII copy, is named Y7954_000466.txt and is 8,388 bytes in size.

FIELD OF THE INVENTION

The present invention relates to a tomato (*Solanum lycopersicum*) plant which is resistant to Tomato brown rugose fruit virus (TBRFV). The invention further relates to a method for producing such *Solanum lycopersicum* plant and methods for identification and selection of such a plant. The invention also relates to progeny, seed and fruit of the Tomato brown rugose fruit virus resistant *Solanum lycopersicum* plant, to propagation material suitable for producing the *Solanum lycopersicum* plant, and to a food product comprising such tomato fruit or part thereof. The invention further relates to a cell or a tissue culture that results from or can be regenerated into a Tomato brown rugose fruit virus resistant *Solanum lycopersicum* plant. The invention also relates to a marker for identification of Tomato brown rugose fruit virus resistant *Solanum lycopersicum* plants, and to use of said marker.

BACKGROUND OF THE INVENTION

One of the problems that is encountered when growing a tomato crop (*Solanum lycopersicum*) is the occurrence of various viruses. Resistance against many known viruses has been identified, which resistances are incorporated in suitable tomato varieties through breeding. This allows the growers to obtain a good yield even when a certain virus is present during production. Regularly however new viruses or strains of known viruses are identified, that in certain instances can break the available resistance.

In 2015 the occurrence of a new tobamovirus in tomato was published (Salem et al: *A new tobamovirus infecting tomato crops in Jordan.* Arch Virol. 2016 February; 161(2): 503-6. Epub 2015 November 19). This virus was shown to be related to the known tobamoviruses Tobacco mosaic virus (TMV), Tomato mosaic virus (ToMV), and Tomato mild mottle virus (ToMMV), with sequence identities of around 80% to 90% for the closest related sequences of ToMMV and ToMV.

Symptoms were rather mild on the plant, but very severe brown rugose symptoms were present on almost all fruits. The virus was observed to break the resistance of the commonly used resistance genes against ToMV: Tm-1, Tm-2, and Tm-2$^2$, which is also known as Tm-2$^a$. A later publication showed that the virus was also found in Israel, and it was established that the virus can also infect pepper (*Capsicum annuum*) plants (Luria et al (2017): *A new Israeli tobamovirus isolate infects tomato plants harboring Tm-2$^2$ resistance genes.* PLoS ONE 12(1):e0170429. Doi:10.1371/journal.pone.0170429). Symptoms appeared to vary based on the affected variety, and in certain instances symptoms were mainly found on the vegetative parts in the form of severe or mild mosaic, necrosis, leaf distortion, or other symptoms. As the virus was clearly different from the known tobamoviruses it was described with a new designation: Tomato brown rugose fruit virus (TBRFV).

Because of the severity of the symptoms on the fruits the impact of the presence of TBRFV on tomato growers is very high, since it leaves the fruits basically unmarketable. No resistance against the virus has been identified so far. The virus is at least transmitted mechanically, which makes the spread easy and rapid, and difficult to control. Transmission of the virus is also likely to occur through infected seed.

SUMMARY OF THE INVENTION

It is an object of the present invention to provide a tomato plant of the species *Solanum lycopersicum* that is resistant to Tomato brown rugose fruit virus (TBRFV).

Because the problems with the new TBRFV spread very quickly and had a major effect on tomato production in certain areas, the urgency to obtain resistant tomato plants was very high. In addition, the virus was expected to be able to spread rapidly to other areas due to its very effective transmission. A large germplasm screen was therefore organized to get an insight in the presence of possible sources.

DEPOSITS

Seed of tomato *Solanum lycopersicum* comprising one or more QTLs of the invention resulting in a TBRFV resistant plant was deposited with NCIMB Ltd, Ferguson Building, Craibstone Estate, Bucksburn, Aberdeen AB21 9YA, UK on Sep. 11, 2017 under deposit accession numbers NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, and NCIMB 42890.

The Deposits with NCIMB Ltd, under deposit accession numbers NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, and NCIMB 42890 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1—Genomic sequences of SEQ ID NOS: 1-25 that can be used as markers, or can be used to develop markers, for the identification of a QTL of the invention.

DETAILED DESCRIPTION OF THE INVENTION

*Solanum lycopersicum* has various wild relatives that harbor disease resistances and are a valuable resource for breeding. Many of the latest tomato varieties therefore already possess one or more introgressions from wild species. However, it appeared that presently cultivated tomato varieties, including the ones that already have tobamovirus resistance genes from wild relatives, were easily infected by this new virus. This could mean it would not be straightforward to identify resistance.

Surprisingly, after extensive screening, three accessions of the species *Solanum pimpinellifolium* could be identified that were highly resistant to TBRFV (Example 1). A research program was subsequently set up to determine if the resistance could be transferred to *Solanum lycopersicum*, and to identify the genetics behind the resistance.

Crosses were made between the three *S. pimpinellifolium* sources GNL.3919, GNL.3920, and GNL.3951 on the one hand, and internal breeding lines, followed by population development, such as F2, F3, and backcross populations, for QTL mapping. On all generations bio-assays were carried out to confirm and monitor the resistance in the various populations, and to determine the inheritance. The identification of a QTL gives the opportunity to use linked markers to identify the presence of the resistance, which is obviously much more efficient than the use of a bio-assay.

For this purpose QTL mapping studies were performed. A first QTL mapping on F2 populations identified a QTL region on chromosome 11, a QTL region on chromosome 12, and a QTL region on chromosome 6. The QTL regions on chromosome 11 and chromosome 12 were present in populations that were developed from all three sources. The QTL region on chromosome 6 was identified in populations developed from source GNL.3951.

The present invention provides a tomato plant that is resistant to Tomato brown rugose fruit virus (TBRFV), which plant comprises a QTL on chromosome 11, and/or a QTL on chromosome 12, and/or a QTL on chromosome 6.

In one embodiment the invention provides a tomato plant that is resistant to TBRFV comprising a QTL on chromosome 11 and a QTL on chromosome 12, or a QTL on chromosome 11 and a QTL on chromosome 6, or a QTL on chromosome 12 and a QTL on chromosome 6, or a QTL on chromosome 11 and a QTL on chromosome 12 and a QTL on chromosome 6.

As used herein, the phrase "a QTL on chromosome 11, and/or a QTL on chromosome 12, and/or a QTL on chromosome 6" comprises a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6.

The QTL on chromosome 11 is located between SEQ ID NO: 1 and SEQ ID NO: 9. The QTL on chromosome 12 is located between SEQ ID NO: 10 and SEQ ID NO: 15. The QTL on chromosome 6 is located between SEQ ID NO: 16 and SEQ ID NO: 25. SEQ ID NOS:. 1 and 9 are suitable for identifying the presence of the QTL on chromosome 11. SEQ ID NOS:. 10 and 15 are suitable for identifying the presence of the QTL on chromosome 12. SEQ ID NOS:. 16 and 25 are suitable for identifying the presence of the QTL on chromosome 6.

A further marker suitable for identifying the presence of the QTL on chromosome 11 is selected from the group comprising SEQ ID NOS:. 2 to 8, or any other polymorphism between susceptible and resistant plants that is located between SEQ ID NO: 1 and SEQ ID NO: 9. A further marker suitable for identifying the presence of the QTL on chromosome 12 is selected from the group comprising SEQ ID NOS:. 11 to 14, or any other polymorphism between susceptible and resistant plants that is located between SEQ ID NO: 10 and SEQ ID NO: 15. A further marker suitable for identifying the presence of the QTL on chromosome 6 is selected from the group comprising SEQ ID NOS:. 17 to 24, or any other polymorphism between susceptible and resistant plants that is located between SEQ ID NO: 16 and SEQ ID NO: 25 (Example 2).

FIG. 1 gives the sequences of the SEQ ID NOS:. that can be used as markers, or used to develop markers, to identify the presence of a QTL leading to TBRFV resistance in a tomato plant. Table 3 shows the marker score that identifies the presence of the QTL, and therefore a resistant plant, as well as the position of the SNP in the sequence of FIG. 1. When the sequences of the markers are positioned on for example version SL3_00 of the publicly available genome reference sequence for *S. lycopersicum*, the physical position to which the SNP polymorphism in said marker sequence corresponds can be derived. Version SL3_00 of the public *S. lycopersicum* genome reference sequence can for example be accessed at the Solgenomics website (solgenomics.net) and is the reference for 'the public tomato genome' as used herein. The positions of the QTLs and the markers of the invention are derivable from a public map and these positions are relative to said physical positions. Identifying the presence of a marker is in particular done by identifying the presence of the nucleotide at the position of the SNP that is indicative for the resistance, as present in any of the sequences determining the SEQ ID NOS:, as compared to the wildtype nucleotide at the position of the SNP; the locations and nucleotide of the SNPs that are indicative for resistance are indicated in Table 3.

As used herein, a tomato plant is a plant of the species *Solanum lycopersicum.*

As used herein, resistance to the Tomato brown rugose fruit virus is resistance to the virus as described in Salem et al (2016, supra), which virus was assigned NCBI Taxonomy ID 1761477.

As used herein a marker is genetically linked to, and can therefore be used for the identification of a QTL of the invention, when the marker and the trait co-segregate in a segregating population resulting from a cross between a plant comprising a QTL of the invention and a plant lacking the QTL.

The TBRFV resistance of the present invention inherits in an incompletely dominant or intermediate manner. As used herein, incompletely dominant or intermediate means that when a QTL of the invention is homozygously present, it gives a higher level of TBRFV resistance than when the QTL of the invention is heterozygously present. The heterozygous presence of a QTL of the invention however still confers a certain level of TBRFV resistance, which can be defined as intermediate resistance or tolerance. The TBRFV resistance of both homozygous and heterozygous plants makes the plants more suitable for cultivation under conditions where TBRFV is present. Therefore both levels of resistance are considered to be improved agronomic characteristics.

The presence of TBRFV resistance can be determined through a bioassay, for example using a standard sap-mechanical inoculation technique for tobamoviruses, which is known to the skilled person, and is also for example described in Luria et al (2017, supra). Observation of the symptoms on the young tomato plants can be done at around 12-18 days after inoculation (dai).

TBRFV resistance is determined by comparison to a control variety known to be TBRFV susceptible. Examples of TBRFV susceptible tomato varieties are Candela F1 and Razymo F1. Since no tomato varieties that are resistant to TBRFV were known yet, it was not possible to include a resistant control before the present invention was done. Resistance is suitably scored on a scale of 0-4; the scales of the scores can be found in Table 1.

TABLE 1

| scales TBRFV resistance scores | |
| --- | --- |
| score | Symptoms |
| 0 | No symptoms |
| 1 | Not clean, a single spot, some minor discoloration |
| 2 | Mosaic, clear visible symptoms |
| 3 | Severe mosaic, starting deformation in the head |
| 4 | Severe mosaic, necrosis on the stem, serious deformation in the head, spots in blisters |

As used herein, a TBRFV resistant tomato plant has a score of 0 or 1 when scoring according to Table 1 is used. A plant comprising one or more QTLs of the invention heterozygously has an intermediate resistance and has a score of 0, 1 or 2.

A *S. lycopersicum* plant that has a QTL of the invention that leads to TBRFV resistance can be grown from seed deposited as NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890. NCIMB 42879, NCIMB 42880, NCIMB 42881, NCIMB 42882, and NCIMB 42883 were developed from GNL.3951. NCIMB 42884, NCIMB 42885, and NCIMB 42886 were developed from GBN.3920. NCIMB 42887, NCIMB 42888, NCIMB 42889, and NCIMB 42890 were developed from GNL.3919.

NCIMB 42879 has the TBRFV resistance of the invention and comprises a QTL on chromosome 11 that can be identified by SEQ ID NOS:. 1 and 9; and/or a QTL on chromosome 12 that can be identified by SEQ ID NOS:. 10 and 15; and/or a QTL on chromosome 6 that can be identified by SEQ ID NOS:. 16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42880 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS:16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42881 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS:16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42882 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS:16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42883 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS:16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42884 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS:16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42885 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS: 16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42886 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS: 16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42887 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS: 16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42888 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS: 16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42889 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS: 16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

NCIMB 42890 has the TBRFV resistance of the invention and comprises a QTL on chromosome 11 that can be identified by SEQ ID NOS: 1 and 9; and/or a QTL on chromosome 12 that can be identified by SEQ ID NOS: 10 and 15; and/or a QTL on chromosome 6 that can be identified by SEQ ID NOS: 16 and 25. A QTL is present in the deposit in homozygous form, or in heterozygous form. The QTL on chromosome 11 can also be identified by determining the presence of at least one of the markers of the group comprising SEQ ID NOS: 2-8. The QTL on chromosome 12 can also be identified by determining the presence of at least one of the markers of the group comprising SEQ ID NOS: 11-14. The QTL on chromosome 6 can also be identified by determining the presence of at least one of the markers of the group comprising SEQ ID NOS: 17-24.

A plant comprising the QTL of the invention on chromosome 11, and/or the QTL of the invention on chromosome 12, and/or the QTL of the invention on chromosome 6, can be used as a resistant control variety in a TBRFV bio-assay. When a plant, line, or population to be assessed shows the same level of resistance as NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890 in a bio-assay, and this plant, line or population comprises a QTL as described herein on chromosome 11, and/or a QTL as described herein on chromosome 12, and/or a QTL as described herein on chromosome 6, this plant, line, or population is considered to have the TBRFV resistance of the invention and is therefore a plant of the invention.

A plant of the present invention is optionally a cultivated *S. lycopersicum* plant having improved agronomic characteristics that make it suitable for commercial cultivation. The invention also relates to a tomato fruit harvested from a plant of the invention, wherein the tomato fruit comprises a QTL of the invention in its genome which leads to TBRFV resistance in the plant. This tomato fruit is also referred to herein as 'the fruit of the invention' or 'the tomato fruit of the invention'. As used herein, 'tomato fruit' comprises a fruit produced by a plant of the species *Solanum lycopersicum*.

The present invention provides a QTL on chromosome 11, which QTL is linked to at least one of the markers represented by SEQ ID NOS: 1, 9, and 2-8, wherein the presence of said QTL in a *S. lycopersicum* plant leads to TBRFV resistance.

The present invention provides a QTL on chromosome 12, which QTL is linked to at least one of the markers represented by SEQ ID NOS: 10, 15, and 11-14, wherein the presence of said QTL in a *S. lycopersicum* plant leads to TBRFV resistance.

The present invention provides a QTL on chromosome 6, which QTL is linked to at least one of the markers represented by SEQ ID NOS: 16, 25, and 17-24, wherein the presence of said QTL in a *S. lycopersicum* plant leads to TBRFV resistance.

The present invention relates to a method for producing a TBRFV resistant *S. lycopersicum* plant comprising introducing a QTL on chromosome 11 that is flanked by SEQ ID NO: 1 and SEQ ID NO: 9 in a *S. lycopersicum* plant, or introducing a QTL on chromosome 12 that is flanked by SEQ ID NO: 10 and SEQ ID NO: 15 in a *S. lycopersicum* plant, or introducing a QTL on chromosome 6 that is flanked by SEQ ID NO: 16 and SEQ ID NO: 25 in a *S. lycopersicum* plant.

A QTL of the invention can be introduced from another plant which comprises the QTL through commonly used breeding techniques, such as crossing and selection, when the plants are sexually compatible. Such introduction can be from a plant of the same species, that usually can be crossed easily, or from a plant of a related species. Difficulties in crossing can be overcome through techniques known in the art such as embryo rescue, or cis-genesis can be applied. Suitably markers as described herein are used to follow the incorporation of the QTL into another plant.

The above method can in particular be used to introduce a QTL of the invention into a plant species that is suitable for incorporation of such genetic information. In a particular embodiment said QTL can be introduced from a *Solanum pimpinellifolium* plant comprising the QTL into a *Solanum lycopersicum* plant lacking the QTL, for example by using standard breeding methods. In another embodiment said QTL can be introduced from a *Solanum lycopersicum* plant comprising the QTL into a *Solanum lycopersicum* plant lacking the QTL using standard breeding methods.

In one embodiment the QTL on chromosome 11 can be introduced from a *Solanum lycopersicum* plant representative seed of which was deposited with the NCIMB under deposit number NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or from the deposited seed of NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or from sexual or vegetative descendants thereof. Introduction of the QTL on chromosome 11 in *Solanum lycopersicum* leads to TBRFV resistance.

In one embodiment the QTL on chromosome 12 can be introduced from a *Solanum lycopersicum* plant representative seed of which was deposited with the NCIMB under deposit number NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or from the deposited seed of NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or from sexual or vegetative descendants thereof. Introduction of the QTL on chromosome 12 in *Solanum lycopersicum* leads to TBRFV resistance.

In one embodiment the QTL on chromosome 6 can be introduced from a *Solanum lycopersicum* plant representative seed of which was deposited with the NCIMB under deposit number NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or from the deposited seeds of NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or from sexual or vegetative descendants thereof. Introduction of the QTL on chromosome 6 in *Solanum lycopersicum* leads to TBRFV resistance.

Alternatively a QTL of the invention can be transferred from another, sexually incompatible, plant, for example by using a transgenic approach. Techniques that can suitably be used comprise general plant transformation techniques known to the skilled person, such as the use of an *Agrobacterium*-mediated transformation method. Genome editing methods such as the use of a CRISPR/Cas system might also be employed to obtain a plant of the invention.

The invention further relates to a plant of the invention comprising a QTL of the invention leading to TBRFV resistance either homozygously or heterozygously, which plant is a plant of an inbred line, a hybrid, a doubled haploid, or a plant of a segregating population. Preferably, the plant of the invention is a non-transgenic plant.

The invention also relates to a *Solanum lycopersicum* seed comprising a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6, wherein the plant grown from the seed is a plant of the invention that is resistant to TBRFV. The invention also relates to seed produced by a plant of the invention. This seed harbors a QTL of the invention, and as such, a plant grown from said seed is a plant of the invention.

Moreover, the invention also relates to a food product or a processed food product comprising the tomato fruit of the invention or part thereof. The food product may have undergone one or more processing steps. Such a processing step might comprise but is not limited to any one of the following treatments or combinations thereof: peeling, cutting, washing, juicing, cooking, cooling or a salad mixture comprising the fruit of the invention. The processed form that is obtained is also part of this invention.

The invention also relates to propagation material suitable for producing a *Solanum lycopersicum* plant of the invention, wherein the propagation material is suitable for sexual reproduction, and is in particular selected from a microspore, pollen, an ovary, an ovule, an embryo sac, and an egg cell; or is suitable for vegetative reproduction, and is in particular selected from a cutting, a root, a stem, a cell, a protoplast; or is suitable for tissue culture of regenerable cells, and is in particular selected from a leaf, pollen, an embryo, a cotyledon, a hypocotyl, a meristematic cell, a root, a root tip, an anther, a flower, a seed, and a stem; wherein the plant produced from the propagation material comprises a QTL of the invention that confers TBRFV resistance. A plant of the invention may be used as a source of the propagation material.

The invention further relates to a cell comprising a QTL of the invention. A cell of the invention can be obtained from, or be present in, a plant of the invention. Such a cell may either be in isolated form, or a part of a complete plant, or from a part thereof, and still constitutes a cell of the invention because such a cell comprises the genetic information that determines a QTL as described herein that leads to TBRFV resistance of a cultivated *S. lycopersicum* plant. Each cell of a plant of the invention carries the genetic information that leads to TBRFV resistance. A cell of the invention may also be a regenerable cell that can regenerate into a new plant of the invention. The presence of the genetic information in this context is the presence of a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6, wherein a QTL is as defined herein.

The invention further relates to plant tissue of a plant of the invention, which comprises a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 as defined herein. The tissue can be undifferentiated tissue or already differentiated tissue. Undifferentiated tissue is for example a stem tip, an anther, a petal, pollen, and can be used in micropropagation to obtain new plantlets that are grown into new plants of the invention. The tissue can also be grown from a cell of the invention.

The invention moreover relates to progeny of a plant, a cell, a tissue, or a seed of the invention, which progeny comprises a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 as defined herein, the presence of which QTL or combination of QTLs leads to TBRFV resistance. Such progeny can in itself be a plant, a cutting, a seed, a cell, or a tissue.

As used herein "progeny" is intended to mean the first and all further descendants from a cross with a plant of the invention, wherein a cross comprises a cross with itself or a cross with another plant, and wherein a descendant that is determined to be progeny comprises a QTL of the invention.

"Progeny" also encompasses a *S. lycopersicum* plant that carries a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 as defined herein, and has the trait of the invention, and is obtained from another plant, or progeny of a plant, of the invention by vegetative propagation or another form of multiplication.

The invention further relates to a part of a *S. lycopersicum* plant of the invention that is suitable for sexual reproduction, which plant part comprises a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 in its genome, which QTL is as defined herein. Such a part is for example selected from the group comprising a microspore, a pollen, an ovary, an ovule, an embryo sac, and an egg cell.

Additionally, the invention relates to a part of a *S. lycopersicum* plant of the invention that is suitable for vegetative reproduction, which is in particular a cutting, a root, a stem, a cell, or a protoplast that comprises a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 in its genome, which QTL is as defined herein. A part of a plant as previously mentioned is considered propagation material. The plant that is produced from the propagation material comprises a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 as defined herein, the presence of which QTL leads to TBRFV resistance.

The invention further relates to tissue culture of a plant of the invention, which is also propagation material and which comprises a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 in its genome, which QTL is as defined herein. The tissue culture comprises regenerable cells. Such tissue culture can be selected or derived from any part of the plant, in particular from a leaf, pollen, an embryo, a cotyledon, a hypocotyl, a meristematic cell, a root, a root tip, an anther, a flower, a seed, or a stem. The tissue culture can be regenerated into a *S. lycopersicum* plant comprising a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 as defined herein, wherein the regenerated *S. lycopersicum* plant expresses the trait of the invention and is also part of the invention.

The invention additionally relates to the use of a plant of the invention in plant breeding. The invention thus also relates to a breeding method for the development of a cultivated *S. lycopersicum* plant that is resistant to TBRFV, wherein a plant comprising a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 as defined herein for conferring said resistance to another plant is used. Seed being representative for a plant that can be used in plant breeding to develop another plant with TBRFV resistance was deposited with the NCIMB under accession numbers NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, and NCIMB 42890.

The invention also concerns the use of a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 as defined herein for the development of Solanum lycopersicum plants that have resistance to TBRFV.

The invention also relates to a marker for the identification of TBRFV resistance in a Solanum lycopersicum plant, which marker is selected from the group comprising SEQ ID NOS: 1, 9, and 2-8 for the identification of the QTL on chromosome 11; or from the group comprising SEQ ID NOS: 10, 15, and 11-14 for the identification of the QTL on chromosome 12; or from the group comprising SEQ ID NOS: 16, 25, and 17-24 for the identification of the QTL on chromosome 6. The use of any of the markers represented by SEQ ID NOS: 1-25 for identification of TBRFV resistance in a Solanum lycopersicum plant is also part of the invention. Any of these markers can also be used to develop other markers for the identification of a QTL leading to TBRFV resistance, which use is also part of the present invention.

The present invention also relates to a method for selecting a TBRFV resistant Solanum lycopersicum plant, comprising identifying the presence of a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6, and selecting a plant that comprises said QTL or combination of QTLs as a TBRFV resistant plant.

Identifying the presence of the QTL on chromosome 11 is suitably done using a marker selected from the group comprising SEQ ID NOS: 1, 9, and 2-8. Identifying the presence of the QTL on chromosome 12 is suitably done using a marker selected from the group comprising SEQ ID NOS: 10, 15, and 11-14. Identifying the presence of the QTL on chromosome 6 is suitably done using a marker selected from the group comprising SEQ ID NOS: 16, 25, and 17-24.

The invention also relates to a method of testing a Solanum lycopersicum plant for the presence in its genome of a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6 conferring TBRFV resistance, comprising detecting the presence of a marker sequence selected from the groups consisting of SEQ ID NOS: 1-9 for chromosome 11; SEQ ID NOS: 10-15 for chromosome 12; and SEQ ID NOS: 16-25 for chromosome 6, or any combination thereof, in the genome of the Solanum lycopersicum plant.

In one embodiment of the invention, the method of testing a Solanum lycopersicum plant for the presence in its genome of a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6, conferring TBRFV resistance further comprises selecting a Solanum lycopersicum plant that comprises said QTL or combination of QTLs as a TBRFV resistant plant.

The invention also relates to a method for the production of a Solanum lycopersicum plant which is resistant to TBRFV, said method comprising:
a) crossing a plant of the invention, which comprises a QTL of the invention, with another plant;
b) optionally performing one or more rounds of selfing and/or crossing of the plant resulting from the cross to obtain a further generation population;
c) selecting from the plant resulting from the cross, or from the further generation population, a plant that comprises a QTL on chromosome 11, and/or a QTL on chromosome 12, and/or a QTL on chromosome 6 as defined herein, which plant is resistant against TBRFV.

Selection of a plant comprising a QTL on chromosome 11, and/or a QTL on chromosome 12, and/or a QTL on chromosome 6 is suitably done by using a molecular marker linked to the QTL, which marker is selected of the group comprising SEQ ID NOS: 1, 9, and 2-8 for the identification of the QTL on chromosome 11; or from the group comprising SEQ ID NOS: 10, 15, and 11-14 for the identification of the QTL on chromosome 12; or from the group comprising SEQ ID NOS: 16, 25, and 17-24 for the identification of the QTL on chromosome 6. The plant can alternatively, or in addition, be phenotypically selected for having resistance to TBRFV, in particular by performing a bio-assay for TBRFV resistance.

In one embodiment of the invention, the plant of the invention used in the method for the production of a Solanum lycopersicum plant which is resistant against TBRFV is a plant grown from seed deposited under NCIMB accession number NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or a progeny plant thereof.

The invention additionally provides for a method of introducing another desired trait into a Solanum lycopersicum plant comprising TBRFV resistance, comprising:
a) crossing a Solanum lycopersicum plant of the invention with a second Solanum lycopersicum plant that comprises the other desired trait to produce F1 progeny;
b) optionally selecting in the F1 for a plant that comprises TBRFV resistance and the other desired trait;
c) crossing the optionally selected F1 progeny with either parent, to produce backcross progeny;
d) selecting backcross progeny comprising TBRFV resistance and the other desired trait; and
e) optionally repeating steps c) and d) one or more times in succession to produce selected fourth or higher backcross progeny that comprises the other desired trait and has resistance to TBRFV.

In one embodiment of the invention, the plant of the invention used in the method of introducing another desired trait into a Solanum lycopersicum plant comprising resistance to TBRFV is a plant grown from seed deposited under NCIMB accession number NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or a progeny plant thereof.

Optionally, selfing steps are performed after any of the crossing or backcrossing steps. Selection of a plant comprising TBRFV resistance and the other desired trait can alternatively be done following any crossing or selfing step of the method. The other desired trait can be selected from, but is not limited to, the following group: resistance to bacterial, fungal or viral diseases, insect or pest resistance, improved germination, plant size, plant type, improved shelf-life, water stress and heat stress tolerance, and male sterility. The invention includes a *Solanum lycopersicum* plant produced by this method and the *Solanum lycopersicum* fruit obtained therefrom.

The invention further relates to a method for the production of a *Solanum lycopersicum* plant comprising a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6, wherein the presence of said QTL or combination of QTLs leads to resistance to TBRFV, by using tissue culture of plant material that comprises a QTL of the invention in its genome.

The invention further relates to a method for the production of a *Solanum lycopersicum* plant comprising a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6, wherein the presence of said QTL or combination of QTLs leads to resistance to TBRFV, by using vegetative reproduction of plant material that comprises a QTL of the invention in its genome.

The invention further provides a method for the production of a *Solanum lycopersicum* plant having resistance to TBRFV as defined herein by using a doubled haploid generation technique to generate a doubled haploid line that homozygously comprises a QTL of the invention and is resistant against TBRFV.

The invention further relates to a method for the production of a *Solanum lycopersicum* plant comprising a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6, wherein the presence of said QTL or combination of QTLs leads to TBRFV resistance, which method comprises growing a seed comprising said QTL or combination of QTLs into the said *Solanum lycopersicum* plant. In one embodiment, the seed used in the method is seed deposited with the NCIMB under deposit number NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, or NCIMB 42890, or progeny seed thereof.

The invention further relates to a method for seed production comprising growing a *Solanum lycopersicum* plant from a seed of the invention, allowing the plant to produce a fruit with seed, harvesting the fruit, and extracting those seed. Production of the seed is suitably done by selfing or by crossing with another plant that is optionally also a plant of the invention. The seed that is so produced has the capability to grow into a plant that is resistant to TBRFV.

The invention further relates to hybrid seed and to a method for producing said hybrid seed, comprising crossing a first parent plant with a second parent plant and harvesting the resultant hybrid seed, wherein the first parent plant and/or the second parent plant is a plant of the invention comprising a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6. The resulting hybrid plant that can be grown from the hybrid seed, comprising said QTL or combination of QTLs, which hybrid plant has resistance to TBRFV, is also a plant of the invention.

It is clear that the parent that provides the trait of the invention is not necessarily a plant grown directly from the deposited seed. The parent can also be a progeny plant from the deposited seed, or a progeny plant from seed that is identified to have obtained the trait of the invention by other means.

Introgression of a QTL of the invention as used herein means introduction of a QTL from a donor plant comprising said QTL into a recipient plant not carrying said QTL by standard breeding techniques, wherein selection for plants comprising a QTL of the invention can be performed phenotypically by means of observation of the resistance to TBRFV, or selection can be performed with the use of markers as defined herein through marker assisted breeding, or combinations of these selection methods. Selection is started in the F1 or any further generation from an initial cross between the recipient plant and the donor plant, followed by either further crossing or selfing, suitably by using markers as identified and defined herein. The skilled person is familiar with creating and using new molecular markers that can be used to identify or are linked to the trait of the invention. Development and use of such markers for identification and selection of plants of the invention is also part of the invention.

he phrase "trait" in the context of this application refers to the phenotype of the *Solanum lycopersicum* plant of the invention, which is resistance to TBRFV. When a *S. lycopersicum* plant exhibits the trait of the invention, its genome comprises a QTL of the invention on chromosome 11, or on chromosome 12, or on chromosome 6, or a QTL of the invention on chromosome 11 and chromosome 12, or a QTL of the invention on chromosome 11 and chromosome 6, or a QTL of the invention on chromosome 12 and chromosome 6, or a QTL of the invention on chromosome 11 and chromosome 12 and chromosome 6, the presence of which QTL or combination of QTLs is causing the trait of the invention. Hence, the "trait of the invention" as used herein is intended to refer to the trait of resistance to TBRFV.

The present invention will be further illustrated in the Examples that follow and that are for illustration purposes only. The Examples are not intended to limit the invention in any way.

EXAMPLES

Example 1: Bio-Assay for TBRFV Resistance and Deposit Development in *S. lycopersicum*

Because of increasing problems due to the presence of the new TBRFV tobamovirus, and the threat that this virus may easily spread over large areas, an extensive germplasm screen was organised. The screen for potentially resistant material was done through a bio-assay. Since the virus is mechanically transmitted, a standard mechanical inoculation technique was used in the bio-assay. No resistant material was known at the time, so it was not possible to include resistant controls. Susceptible controls were however easy to include; Candela F1 was included as it was published to be susceptible, and Razymo F1 was also included as a second susceptible control. To determine if perhaps resistance was already present in cultivated material, a large number of commercially available hybrid tomato varieties was also included.

Seed of the accessions to be tested was sown in standard seedling trays and 11 seedlings per accession were inoculated 3 weeks after sowing. Scoring of the symptoms was done according to Table 1; at 2 weeks after inoculation, and again at 3 weeks after inoculation.

Inoculum was prepared by grounding leaves of tomato plants that were infected with TBRFV in a 0.01 M phosphate buffer (pH 7.0) mixed with celite. Plants were dusted with carborundum powder prior to gently rubbing the leaf with inoculum.

In the large screen, three *Solanum pimpinellifolium* accessions GNL.3919, GNL.3920, and GNL.3951, were identified to be resistant to TBRFV. All three accessions were 100% resistant, showing no symptoms so having score 0, in the first as well as the second observation. For Candela F1 and Razymo F1, all plants had a score of 4, and they are therefore highly susceptible. The other commercial tomato varieties that were included had mainly scores 3 and 4, and none showed resistant plants.

The identified resistant *S. pimpinellifolium* sources were crossed with internal *S. lycopersicum lines* TB1, TB2, and TO1. F1 plants from these crosses were subsequently grown and F2 seeds were also obtained. A new large screen was set-up again including the sources, the breeding lines, the F1's and 184 F2 plants per population. Average scores of parents and F1's of this screen at two weeks after inoculation can be found in Table 2. The scores of the individual F2 plants segregated as expected and therefore ranged from scores 0 to 4. When plants scored a 3 at the first observation, as was the case for the breeding lines, the plants were removed and a second observation was not done.

From the segregating F2 populations resistant plants were chosen and selfed. Using the parallel developed markers from the QTL analysis (see Example 2), plants were selected that had the identified QTLs. Seeds from these individual plants, in which all three sources were represented, were subsequently deposited as NCIMB 42879, NCIMB 42880, NCIMB 42881, NCIMB 42882, NCIMB 42883, NCIMB 42884, NCIMB 42885, NCIMB 42886, NCIMB 42887, NCIMB 42888, NCIMB 42889, and NCIMB 42890. NCIMB 42879, NCIMB 42880, NCIMB 42881, NCIMB 42882, and NCIMB 42883 were developed from crosses with GNL.3951. NCIMB 42884, NCIMB 42885, and NCIMB 42886 were developed from crosses with GNL.3920. NCIMB 42887, NCIMB 42888, NCIMB 42889, and NCIMB 42890 were developed from crosses with GNL.3919.

TABLE 2

| | TBRFV bio-assay results | |
| --- | --- | --- |
| Number | | Average line or F1 score |
| TB1 | F8 | 3 |
| TB2 | F9 | 3 |

TABLE 2-continued

| | TBRFV bio-assay results | |
| --- | --- | --- |
| Number | | Average line or F1 score |
| TO1 | F9 | 3 |
| GNL.3920 | F6 | 0.5 |
| GNL.3951 | F6 | 0.5 |
| GNL.3919 | F6 | 0.5 |
| (TB1 × GNL.3920) | F1 | 1.0 |
| (TB2 × GNL.3920) | F1 | 3.0 |
| (TO1 × GNL.3920) | F1 | 0.5 |
| (TB1 × GNL.3951) | F1 | 1.0 |
| (TB2 × GNL.3951) | F1 | 3.5 |
| (TO1 × GNL.3951) | F1 | 1.5 |
| (TB1 × GNL.3919) | F1 | 0.5 |
| (TB2 × GNL.3919) | F1 | 2.4 |
| (TO1 × GNL.3919) | F1 | 0.5 |

Example 2: QTL Mapping and Marker Development

In order to map TBRFV resistance conferring QTLs from the identified sources, 184 plants of the F2 populations of 7 F1's from Table 2 were phenotyped for TBRFV resistance; parents were also included for reference; DNA samples were taken of each plant for genotyping. Phenotypic scores 0 to 4 according to Table 1 were present in all F2 populations.

Per population a genetic map was constructed; non-polymorphic markers and markers with a strong segregation distortion were removed. For each population around 400 to 450 markers were mapped that were well-distributed over the genome with an average spacing of 2-3 cM. The marker order was determined; the public genome assembly was used to determine numbering and orientation of the linkage groups. From the seven individual maps a consensus map was created.

Phenotypic scores, genotypic data, and the consensus map containing marker positions were used as input data for the QTL mapping. QTL analysis was performed, and mapping of the data resulted in the identification of three QTLs: one on chromosome 11, one on chromosome 12, and one on chromosome 6. Polymorphic SNP markers that were identified in this analysis and can be used to detect these QTLs are presented in Table 3. The sequences of these markers are given in FIG. 1. These markers can be used to identify the presence of a QTL in plants grown from the deposits. These markers can further be used to identify the presence of a QTL for TBRFV resistance on chromosome 11, 12, or 6 in any other population that comprises said QTL.

TABLE 3

| | SNP markers | | | |
| --- | --- | --- | --- | --- |
| Marker name | QTL on chromosome | position of the SNP in the sequence of FIG. 1 | Nucleotide of the SNP in FIG. 1, to be used as marker of the invention | Nucleotide of the SNP in the wildtype (susceptible allele) |
| SEQ ID NO: 1 | 11 | 101 | G | A |
| SEQ ID NO: 2 | 11 | 101 | T | C |
| SEQ ID NO: 3 | 11 | 101 | G | A |
| SEQ ID NO: 4 | 11 | 101 | G | A |
| SEQ ID NO: 5 | 11 | 101 | A | G |
| SEQ ID NO: 6 | 11 | 101 | G | A |
| SEQ ID NO: 7 | 11 | 101 | T | C |
| SEQ ID NO: 8 | 11 | 101 | G | A |
| SEQ ID NO: 9 | 11 | 101 | A | G |
| SEQ ID NO: 10 | 12 | 61 | A | G |
| SEQ ID NO: 11 | 12 | 61 | G | A |

TABLE 3-continued

| SNP markers | | | | |
|---|---|---|---|---|
| Marker name | QTL on chromosome | position of the SNP in the sequence of FIG. 1 | Nucleotide of the SNP in FIG. 1, to be used as marker of the invention | Nucleotide of the SNP in the wildtype (susceptible allele) |
| SEQ ID NO: 12 | 12 | 60 | G | A |
| SEQ ID NO: 13 | 12 | 61 | G | A |
| SEQ ID NO: 14 | 12 | 61 | A | G |
| SEQ ID NO: 15 | 12 | 61 | A | G |
| SEQ ID NO: 16 | 6 | 101 | A | G |
| SEQ ID NO: 17 | 6 | 23 | T | C |
| SEQ ID NO: 18 | 6 | 50 | C | T |
| SEQ ID NO: 19 | 6 | 61 | A | G |

TABLE 3-continued

| SNP markers | | | | |
|---|---|---|---|---|
| Marker name | QTL on chromosome | position of the SNP in the sequence of FIG. 1 | Nucleotide of the SNP in FIG. 1, to be used as marker of the invention | Nucleotide of the SNP in the wildtype (susceptible allele) |
| SEQ ID NO: 20 | 6 | 101 | G | A |
| SEQ ID NO: 21 | 6 | 61 | T | C |
| SEQ ID NO: 22 | 6 | 61 | C | A |
| SEQ ID NO: 23 | 6 | 61 | A | G |
| SEQ ID NO: 24 | 6 | 61 | C | T |
| SEQ ID NO: 25 | 6 | 101 | G | A |

The invention claimed is:

1. A *Solanum lycopersicum* plant that is resistant to Tomato brown rugose fruit virus (TBRFV), which plant comprises a QTL on chromosome 11 and a QTL on chromosome 12, wherein the QTL on chromosome 11 is located between SEQ ID NOS. 1 and 9 and linked to co-segregating markers having the sequences of SEQ ID NOs: 4 and 5; and the QTL on chromosome 12 is located between SEQ ID NOS. 10 and 15 and linked to co-segregating markers having the sequences of SEQ ID NOs: 12, 13, and 14, wherein the QTL on chromosome 11 and the QTL on chromosome 12 are as comprised on chromosome 11 having the sequences of SEQ ID NOs: 4 and 5, and chromosome 12 having the sequences of SEQ ID NOs: 12, 13, and 14 in the genome of a *Solanum lycopersicum* plant, representative seed of which was deposited with the NCIMB under deposit number NCIMB 42885 and NCIMB 42887, and wherein the QTL on chromosome 11 and the QTL on chromosome 12 confer resistance to TBRFV.

2. A cell of the TBRFV resistant *Solanum lycopersicum* plant as claimed in claim 1, which cell comprises the QTL as defined in the plant of claim 1 on chromosome 11 and the QTL as defined in the plant of claim 1 on chromosome 12 in its genome.

3. A seed, wherein a plant grown from the seed is resistant to TBRFV due to the presence in its genome of the QTL as defined in the plant of claim 1 on chromosome 11 and the QTL as defined in the plant of claim 1 on chromosome 12.

4. A propagation material that produces the *Solanum lycopersicum* plant as claimed in claim 1, wherein the propagation material is for sexual reproduction, and is selected from a microspore, pollen, an ovary, an ovule, an embryo sac, and an egg cell; or is suitable for vegetative reproduction, wherein the propagation material is for vegetative reproduction, and is selected from a cutting, a root, a stem, a cell, and a protoplast, or wherein the propagation material is for tissue culture of regenerable cells, and is selected from a leaf, pollen, an embryo, a cotyledon, a hypocotyl, a meristematic cell, a root, a root tip, an anther, a flower, a seed, and a stem, and wherein the propagation material and the plant produced from the propagation material comprise the QTL that confers TBRFV resistance on chromosome 11 and the QTL that confers TBRFV resistance on chromosome 12 as defined in the plant of claim 1.

* * * * *